(12) United States Patent
Göhler et al.

(10) Patent No.: US 10,123,713 B2
(45) Date of Patent: Nov. 13, 2018

(54) PATIENT DATA SENSOR DEVICE (75) Inventors: Karlheinz Göhler, Zwönitz (DE); Gerd Kunze, Zwönitz (DE); Christian Von Falkenhausen, Meckenheim (DE)

(73) Assignee: RAUMEDIC AG, Münchberg (DE)

( * ) Notice: Subject to any disclaimer, the term of this patent is extended or adjusted under 35 U.S.C. 154(b) by 570 days.

(21) Appl. No.: 12/920,288

(22) PCT Filed: Feb. 24, 2009

(86) PCT No.: PCT/EP2009/001284
§ 371 (c)(1),
(2), (4) Date: Aug. 30, 2010

(87) PCT Pub. No.: WO2009/106284
PCT Pub. Date: Sep. 3, 2009

(65) Prior Publication Data
US 2011/0009716 A1 Jan. 13, 2011

(30) Foreign Application Priority Data
Feb. 28, 2008 (DE) .......................... 10 2008 011 601

(51) Int. Cl.
*A61B 5/00* (2006.01)
*A61B 5/03* (2006.01)
(Continued)

(52) U.S. Cl.
CPC ............ *A61B 5/031* (2013.01); *A61B 5/0031* (2013.01); *A61B 5/6864* (2013.01);
(Continued)

(58) Field of Classification Search
CPC ........................ A61B 5/0476; A61B 5/0482
(Continued)

(56) References Cited

U.S. PATENT DOCUMENTS

| 4,127,110 A | 11/1978 | Bullara |
| 5,862,803 A * | 1/1999 | Besson et al. ............... 600/508 |

(Continued)

FOREIGN PATENT DOCUMENTS

| CN | 101959448 | 1/2011 |
| DE | 19638813 C1 | 3/1998 |

(Continued)

OTHER PUBLICATIONS

MINCO Flex-Circuit Design Guide, Application Aid #24, Mar. 2000, www.minco.com.*

(Continued)

*Primary Examiner* — Christian Jang
(74) *Attorney, Agent, or Firm* — Browdy and Neimark, PLLC (57) ABSTRACT A patient data sensor device has an implantable patient data sensor and an implantable data transmission mechanism, which is in signal connection with the patient data sensor. The data transmission mechanism has an antenna for telemetric data transmission to an external data collection unit. In addition, the data transmission mechanism has a carrier plate for electronic components. The latter are covered on the carrier plate, at least to one side, by a cover. The antenna is configured in an edge region of the carrier plate and running around the latter and around the electronic components. The result is a patient data sensor device which is more tolerable for the patient.

12 Claims, 5 Drawing Sheets

(51) Int. Cl.
*H01Q 1/22* (2006.01)
*H01Q 1/27* (2006.01)
*H05K 1/16* (2006.01)

(52) U.S. Cl.
CPC ........... *H01Q 1/2208* (2013.01); *H01Q 1/273* (2013.01); *H05K 1/16* (2013.01); *H05K 2201/09027* (2013.01)

(58) Field of Classification Search
USPC .................................................. 600/302, 435
See application file for complete search history.

(56) References Cited

U.S. PATENT DOCUMENTS

| | | | |
|---|---|---|---|
| 5,951,487 A | 9/1999 | Brehmeier-Flick et al. | |
| 5,951,594 A * | 9/1999 | Kerver | 607/32 |
| 6,083,174 A | 7/2000 | Brehmeier-Flick et al. | |
| 6,560,471 B1 * | 5/2003 | Heller | A61B 5/0002 600/309 |
| 6,560,486 B1 * | 5/2003 | Osorio et al. | 607/45 |
| 6,606,247 B2 * | 8/2003 | Credelle et al. | 361/737 |
| 6,718,203 B2 * | 4/2004 | Weiner et al. | 607/2 |
| 7,289,855 B2 | 10/2007 | Nghiem et al. | |
| 2002/0107436 A1 | 8/2002 | Barton et al. | |
| 2002/0149521 A1 * | 10/2002 | Hendler et al. | 343/700 MS |
| 2004/0049121 A1 * | 3/2004 | Yaron | 600/544 |
| 2004/0082977 A1 * | 4/2004 | Engmark et al. | 607/36 |
| 2004/0193020 A1 | 9/2004 | Chiba et al. | |
| 2004/0209396 A1 * | 10/2004 | Krulevitch | A61N 1/0452 438/106 |
| 2006/0025704 A1 * | 2/2006 | Stendel et al. | 600/561 |
| 2006/0241422 A1 * | 10/2006 | Muratayev et al. | 600/435 |
| 2007/0161919 A1 * | 7/2007 | DiLorenzo | 600/544 |
| 2007/0208235 A1 | 9/2007 | Besson et al. | |
| 2008/0139959 A1 | 6/2008 | Miethke et al. | |

FOREIGN PATENT DOCUMENTS

| | | |
|---|---|---|
| DE | 19705474 A1 | 8/1998 |
| DE | 10156469 A1 | 6/2003 |
| DE | 10239743 A1 | 3/2004 |
| DE | 10353144 A1 | 6/2005 |
| DE | 102005020569 A1 | 11/2006 |
| DE | 102006020862 A1 | 7/2007 |
| RU | 1827270 A1 | 7/1993 |
| WO | WO02062215 A2 | 8/2002 |
| WO | 2006/089607 | 8/2006 |

OTHER PUBLICATIONS

Office Action cited by the Russian Patent Office in application RU 2010 131 847 dated Dec. 13, 2011.
English Translation of Chinese Office Action of Appln. No. 200980106760.8 dated May 28, 2013.

* cited by examiner

PATIENT DATA SENSOR DEVICE

FIELD OF THE INVENTION

The invention relates to a patient data sensor device with an implantable patient data sensor, with an implantable data transmission mechanism, which is in signal connection with the patient data sensor, wherein the data transmission mechanism has an antenna for telemetric data transmission to an external data collection unit and a carrier plate for electronic components, wherein the electronic components on the carrier plate are covered at least to one side by a cover.

BACKGROUND OF THE INVENTION

A sensor device of this type is known from DE 102 39 743 A1 as a brain parameter sensor device. Further sensor devices are known from WO 02/062215 A2, U.S. 2006/0020300 A1, U.S. Pat. No. 6,083,174, DE 197 05 474 A1, DE 196 38 813 C1, DE 101 56 469 A1 and DE 103 53 144 A1. The known sensor devices, to the extent that they have a carrier plate with electronic components, are structurally large in such a way that they are experienced as annoying by the patient following implantation. In addition, there is a risk of a post-operative infection.

SUMMARY OF THE INVENTION

It is therefore an object of the present invention, to develop a patient data sensor device of the type mentioned at the outset such that it is more tolerable for the patient.

The object is achieved according to the invention by a patient data sensor device in which the antenna is arranged in an edge region of the carrier plate and is configured running around the latter and around the electronic components.

According to the invention it was recognised that a peripheral arrangement of the antenna produces a saving of installation space on the carrier plate, which can be used to accommodate components, so the installation space requirement of the carrier plate in total, on which these electronic components have to be carried, is reduced. Accordingly, the carrier plate and therefore the part of the sensor device with a significant overall height can be compact. The peripheral antenna may easily be configured so flat that it does not disturb the patient when implanted. The components may then be arranged on the carrier plate in such a way that rigid edges, which entail a pressure on the scalp and therefore a risk of infection, are avoided. The sensor device may, in particular, be configured in such a way that milling out of the cranial bone to implant the sensor device can be dispensed with. The outer peripheral arrangement of the antenna also leads to an improvement in the data transmission, as the large antenna diameter, in comparison to the prior art, provides transmission advantages. In addition, an overlapping of the antenna with the other electronic components, which would lead to interference in the transmission, is avoided. In the outer region of the sensor device predetermined by the antenna, the scalp only has to be lifted minimally from the cranial bone during implantation of the sensor device. The signal connection between the data transmission mechanism and the patient sensor is, in particular, cable-bound, but may, in principle, also be wireless. The cover is convex, at least in the region, where it represents the highest elevation above the carrier plate. Normally, this is a central portion of the cover. Edge regions of the cover, in particular where the latter is connected to the carrier plate, may also be concave. The terms "convex" and "concave" in this case always relate to the design of an outer wall of the cover. The patient data sensor device may, in particular, be configured as a brain parameter sensor device. The patient data sensor is then a brain parameter sensor. A flexible carrier layer of the carrier plate may be produced from polyimide (PI).

In a cover formed convexly at least in portions and covering the electronic components on the carrier plate toward both sides at, there is a possibility of equipping the carrier plates on the two sides with electronic components. This again reduces the surface requirement for the carrier plate and therefore for the sensor device.

If the antenna is configured as a part of a flexible antenna layer, which is connected in a planar manner to the carrier plate and surrounds the latter at the edge, the sensor device in the outer region may be adapted, in terms of shape, when implanted, to the cranial bone, on which the sensor device rests. This again increases the wearing comfort of the sensor device. The antenna layer is, in particular, connected to a flexible portion of the carrier plate.

A circular antenna layer leads to a symmetrisation in relation to the telemetric data transmission, which facilitates the coupling of the external data collection unit.

A configuration of the carrier plate in two layers with two carrier layers, between which the antenna layer is arranged, simplifies the attachment of the antenna layer. Alternatively, the carrier plate may also be configured in one layer.

An arrangement in which the at least one cover is connected to a flexible carrier layer of the carrier plate, increases the flexibility and therefore the shape adaptability of the sensor device.

A configuration of the antenna as a printed circuit is economical and compact. Alternatively, the antenna may also be formed by at least one winding wire, which is configured running round the electronic components.

A coating or embedding made of biocompatible material and covering the carrier plate, where it would be accessible from the outside, reduces the material requirements of the carrier plate. The cover for the electronic components on the carrier plate may also be provided with the same coating or embedding. The coating or cover may simultaneously ensure a tightness of the sensor device, so no fluid can penetrate to the electronic components of the sensor device. The coating or cover may also ensure a desired electric insulation of the antenna.

Biocompatible materials for the coating or embedding such as silicone, silicone rubber, parylene or of polyurethane have proven to be particularly suitable.

This applies accordingly to cover materials such as ceramic or titanium.

A thickness ratio, in which the carrier plate, in an edge region carrying the antenna, has a plate thickness, which is at most half a thickness measured in the same direction of a region of the carrier plate carrying the electronic components, assuming a certain basic flexibility of the material of the carrier plate, leads to an increased flexibility of the carrier plate, which is then thinner in the edge region. A configuration of this type may then lead to a sensor device which is flexible as a whole in the edge region, which again improves the adaptability and therefore the wearing comfort of the sensor device. With this thickness ratio, the sensor device is also experienced as least annoying by the patient in the edge region, in other words where it has the greatest lateral extent, because of its thickness, which is then small at the edge.

Embodiments of the invention will be described in more detail below with the aid of the drawings.

DESCRIPTION OF THE PREFERRED EMBODIMENTS

A brain parameter sensor device 1, as an example of a patient data sensor device, has an implantable brain parameter sensor 2 as an example of a patient data sensor. The latter is used, for example, to measure intracranial pressure, for example in the parenchyma or in the ventricles. The sensor 2, alternatively or additionally may also be configured as a temperature sensor. In this case, the sensor 2 may have a Wheatstone bridge. In this case, the ohmic resistance of the bridge diagonal is measured, in particular, which clearly correlates with the temperature to be determined. The sensor 2 is connected to a carrier assembly 4 by means of a catheter tube 3, which may be rigid or flexible. The catheter tube 3 is made of plastics material. Signal and supply lines, not shown in FIG. 1, run in the catheter tube 3, on the one hand, for the energy supply of the sensor 2 and, on the other hand, for signal transmission, in particular for transmitting measurement and control signals. In principle it is possible, instead of the catheter tube 3, to also provide a wireless connection between the sensor 2 and the carrier assembly 4.

Figure 1:
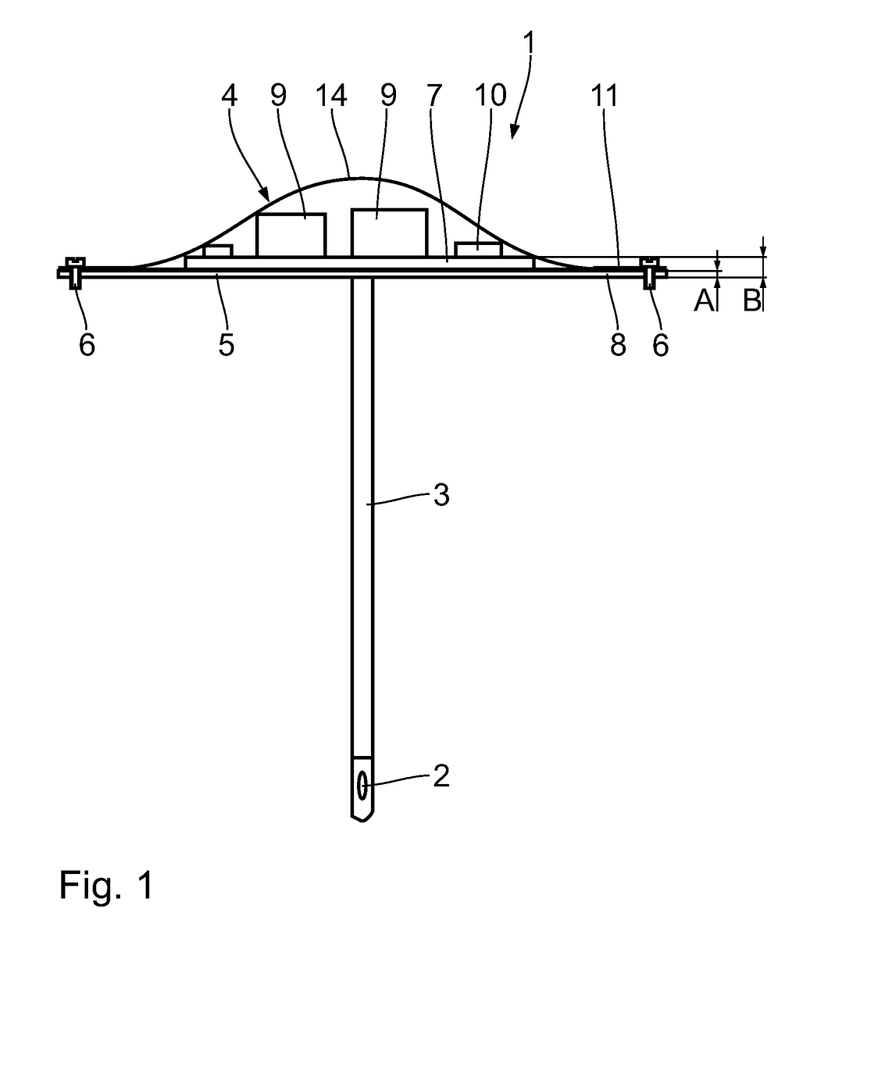
FIG. 1 schematically shows an internal side view giving details of a patient data sensor device using the example of a brain parameter sensor device.

The carrier assembly 4 is placed on a cranial bone, not shown in the drawing, of a patient and fixed. The catheter tube 3 with the sensor 2 is guided through a corresponding bore through the cranial bone until the measurement position is reached. The measurement position may, in this case, be implemented subdurally or epidurally.

In the implanted state, a flexible board 5 with a thickness of about 1 mm faces the cranial bone. The flexible board 5 has the shape of a round disc. The board 5 can be fixed to the cranial bone by means of screws 6. The screws 6 can be guided through fixing tabs in the flexible board 5. The flexible board 5 is part of a carrier plate of a carrier assembly 4. The board 5 has a thickness, which is designated A in FIG. 1.

A rigid board 7, to which electronic components are attached, is placed on the flexible board 5 and connected thereto.

The rigid board 7 has the shape of a round disc, the diameter of which is smaller than that of the flexible board 5. The two boards 5, 7 are arranged concentrically with respect to one another, so the flexible board 5 in a peripheral, annular edge region 8 projects over the rigid board 7. The rigid board 7 has a thickness, which is designated B in FIG. 1.

The two boards 5, 7 are two carrier layers of the carrier plate of the sensor device 1. The flexible printer circuit board 5 is, in particular, laminated onto the rigid board 7. The flexible board 5 is a PCB (Printed Circuit Board). The rigid board 7 is made of the material FR4.

For the thickness ratio A/B there applies: A≤0.5 B. In the edge region 8, the carrier plate 5, 7 thus has a plate thickness A, which is at most half the thickness B measured in the same direction of the region of the carrier plate 5, 7 carrying the electronic components 9, 10.

Structurally high SMD components 9, which are accommodated close to the centre of the rigid board 7, belong to the electronic components. Further, flat electronic components 10 are arranged on the rigid board 7 in the edge region 8 of the rigid board 7. The components 9, 10 are electronic components of the sensor device 1. These components 9, 10 are used for the electric supply of the sensor 2 and for telemetric data exchange between the sensor 2 and an external reading and control mechanism, which is not shown in the drawing. The reading and control mechanism is an external data collection unit. Because of its telemetry function, the carrier assembly 4 is also called a telemetry unit or data transmission mechanism. In addition, the telemetry unit is responsible for the conditioning of the measurement data collected by the sensor 2. This signal conditioning takes place in an application specific integrated circuit (ASIC). A sensor type of the sensor 2 is directly connected to the ASIC by means of a micro cable running in the catheter tube. The ASIC is used, inter alia, as a multiplexer, i.e. as a switching network or as a change-over switch, as an A/D converter and as a serial interface. In the signal or measurement value conditioning, a pressure signal voltage and a bridge diagonal resistance of the Wheatstone bridge are measured cyclically with the sensor 2. For this purpose, sensor lines are periodically switched over on the carrier plate 5, 7 with the aid of the multiplex function of the ASIC. The analogue signal values requested after the multiplexing are passed to the A/D converter and converted there into a digital measurement data signal. This is provided by means of the serial interface of the ASIC for further processing.

The telemetry unit may be configured as a passive transponder, in other words it does not inevitably need its own energy supply.

Figure 2:
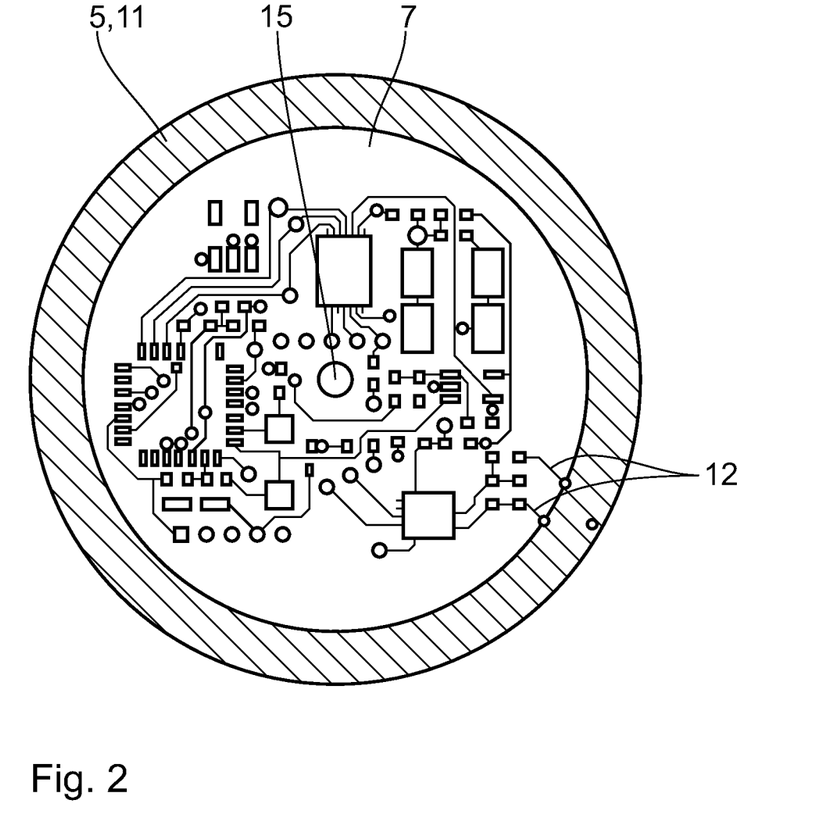
FIG. 2 shows a plan view of the sensor device according to FIG. 1

Provided on the edge region 8 of the flexible board 5 is a thin, annular antenna layer, which predetermines an antenna coil 11 running around the flexible board 5 (c.f. FIG. 2). The antenna coil 11 is thus located on the edge region 8 running around the carrier plate 5, 7. The antenna coil 11 is thus connected in a planar manner to the carrier plate 5, 7. The antenna coil is configured as a printed circuit. The antenna coil or antenna layer is arranged between the two carrier layers of the carrier plate, which are formed by the boards 5, 7. The antenna coil 11 may also have more than one layer. Bonding contacts 12 connect the antenna coil 11 to associated components on the rigid board 7. As the antenna coil 11 is provided on the flexible board 5, this outer antenna region of the sensor device 1 is configured to be thin and flexible.

A telemetric data transmission takes place by means of the antenna coil 11 between the sensor device 1 and the external reading and control mechanism.

When implanted, the sensor device 1 is accommodated underneath the scalp of the patient. Toward the scalp, the sensor device 1 is covered by a cover in the form of a flexible membrane 14. The outer wall of the membrane 14 has an aspherical and convex shape, in other words is clearly flattened compared to a spherical shape. Overall, the part of the sensor device 1, which is arranged, when implanted, on the cranial bone, is so flat that no undesirably high tensions of the scalp occur. The flexible membrane 14 also leads to the fact that the sensor device 1 also does not have sharp edges in the region of the components 9, 10 on the side facing the scalp.

A connection 15 for mechanical and electric coupling of the catheter tube 3 to the carrier plate 5, 7 is provided centrally in the carrier plate 5, 7.

Figure 3:
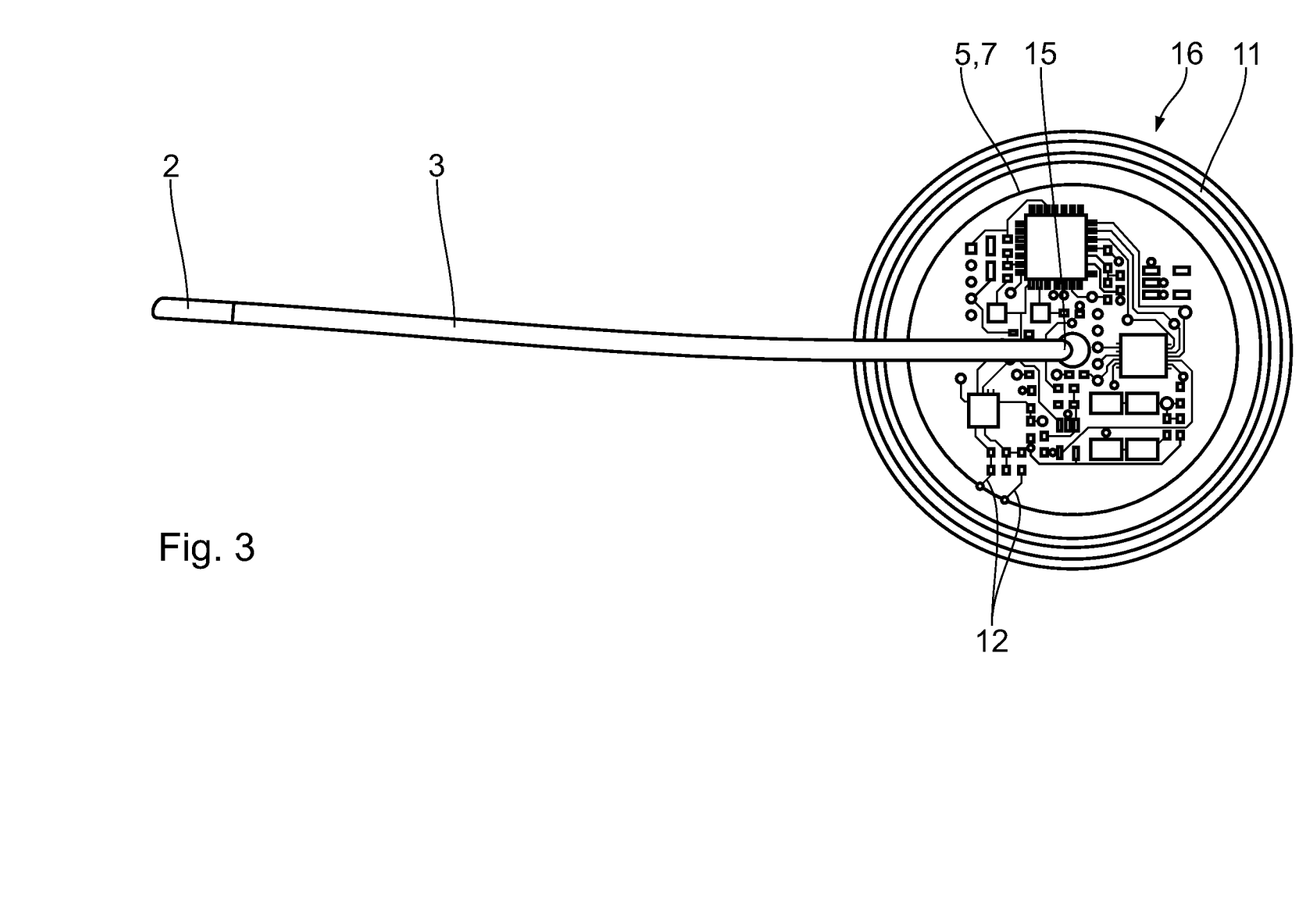
FIG. 3 shows a plan view of a further configuration of a brain parameter sensor device.

FIG. 3 shows a further configuration of a brain parameter sensor device 16. Components, which correspond to those which have already been described above with reference to FIGS. 1 and 2, have the same reference numerals and will not be discussed again in detail.

In the embodiment of the sensor device 16, the catheter tube 3 is guided away laterally from the carrier plate 5, 7, in other words firstly runs adjacent to the carrier plate 5, 7 in a carrier plane predetermined thereby. The catheter tube 3 is so flexible that, when implanted, it is guided, bent in approximately an S-shape, through a correspondingly configured opening in the cranium through the latter, in particular for an epidural measurement. The catheter tube 3 guided out laterally does not interrupt the antenna coil 11 in the configuration according to FIG. 3, but, in the orientation according to FIG. 3, facing the observer, is offset with respect to the antenna coil 11, in other words displaced above the antenna coil 11.

In the configurations according to FIGS. 1 to 3, the flexible board 5 is about 20% larger in diameter than the rigid board 7. The rigid board 7, with regard to its absolute diameter, may be configured still smaller than in FIGS. 1 to 3, so a still greater diameter ratio is possible between the flexible board 5 and the rigid board 7. The reduction in the diameter of the rigid board 7 can be achieved by equipping the rigid board 7 on both sides with components 9, 10. In this case, the flexible board 5 has corresponding recesses at the locations on the back of the rigid board 7, where components 9, 10 are accommodated.

If the rigid board 7 is equipped with components 9, 10 on both sides, the result is, with regard to the carrier assembly 4 in its cross sectional contour in accordance with FIG. 1, a configuration which is substantially mirror-symmetrical about the plane of the carrier plate 5, 7 and approximately ventricular, with two flexible membranes 14 covering the carrier plate 5, 7 and the components 9, 10 provided there on both sides.

Instead of the membrane 14, in the configuration according to FIGS. 1 to 3, a cover which is also formed convexly and made of ceramic or titanium, may also be provided.

Figure 4:
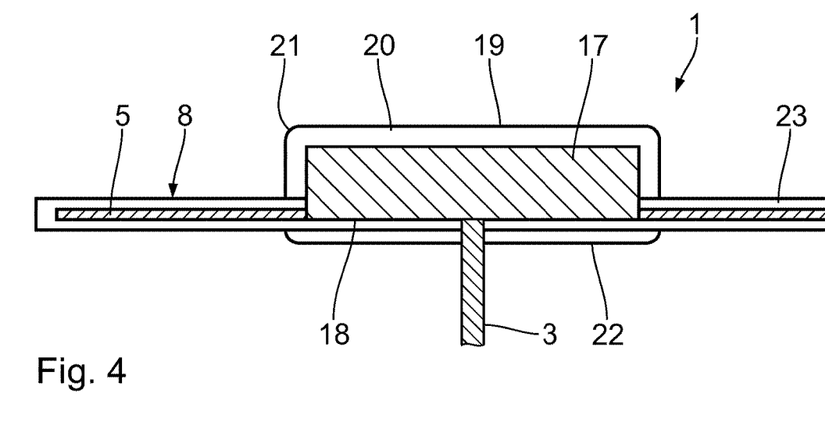
FIG. 4 shows a further configuration of a brain parameter sensor device in a view similar to FIG. 1 and broken in the region of a brain parameter sensor.
Figure 5:
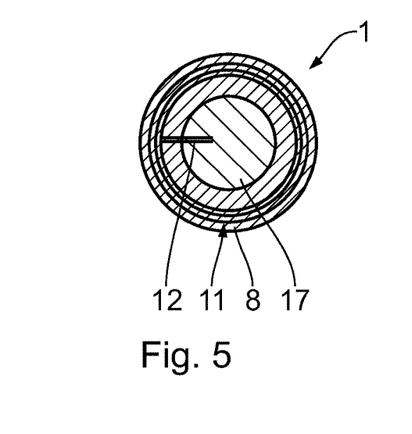
FIG. 5 shows a plan view of the sensor device according to FIG. 4 to a reduced scale in comparison to FIG. 4.

FIGS. 4 and 5 show a further configuration of a brain parameter sensor device 1. Components which correspond to those which have already been described above with respect to FIGS. 1 to 3, have the same reference numerals and will not be discussed again in detail.

In the configuration according to FIG. 4, the rigid board and the components of the configuration according to FIGS. 1 to 3 are combined to form an inner electronics housing 17, which is also designated an electronics board. The electronics housing 17 has the shape of a flat cylinder with dimension ratios of the cylinder height and cylinder diameter, which are comparable with an ice hockey puck reduced in scale.

The flexible board 5, which is also called an antenna board, projects laterally over a base face 18 of the electronics housing 17. The antenna coil 11, as in the configuration according to FIGS. 1 to 3, is attached to the flexible board 5 and not shown in FIG. 4. The antenna coil 11 may be configured in the form of windings printed onto the flexible board 5 or in the form of separate winding wires. This projection of the flexible board 5 corresponds to the projection of the flexible board over the rigid board in the configuration according to FIGS. 1 to 3. The inner electronics housing 17 is surrounded by an outer cover housing 19, which has the function of the membrane 14 in the configuration according to FIGS. 1 to 3.

The outer cover housing 19 has a shell-shaped cover 20 made of ceramic or titanium, which is complementary to the portion of the electronics housing 17 projecting upwardly above the flexible board 5 in FIG. 4. A cover wall of the shell-shaped cover 20 covering the inner electronics housing 17 at the top passes via an annular rounded edge 21 into a sleeve-like side wall of the shell-shaped cover 20, which extends up to the flexible board 5.

Apart from the upper shell-shaped cover 20 in FIG. 4, the cover housing 19 may also have a round counter-cover 22, also made of ceramic or titanium, shown at the bottom in FIG. 4. The latter has a central through-opening for a brain parameter sensor 2. An annular passage for the flexible board 5 remains around the cylinder jacket wall of the electronics housing 17 between the shell-shaped cover 20 and the counter-cover 22.

The flexible board 5 is embedded in a biocompatible embedding 23, which, in the configuration according to FIGS. 4 and 5 is configured as a coating of the flexible board made of silicone, silicone rubber or polyurethane. A coating made of parylene is also possible. The embedding 23 ensures that a patient contact with the sensor device 1 is possible exclusively via the cover housing 19, via the embedding 23 and via the brain parameter sensor 2. The embedding 23 seals the flexible board 5 against the cover housing 19. The biocompatible embedding 23, which is attached in FIG. 4 as a layer below the flexible board 5, seals against the catheter tube 3 of the sensor 2.

A further configuration of a brain parameter sensor device will be described below with the aid of FIG. 6. Components, which correspond to those which have been described above with reference to the configurations according to FIGS. 1 to 5, have the same reference numerals and will not be discussed again in detail.

Figure 6:
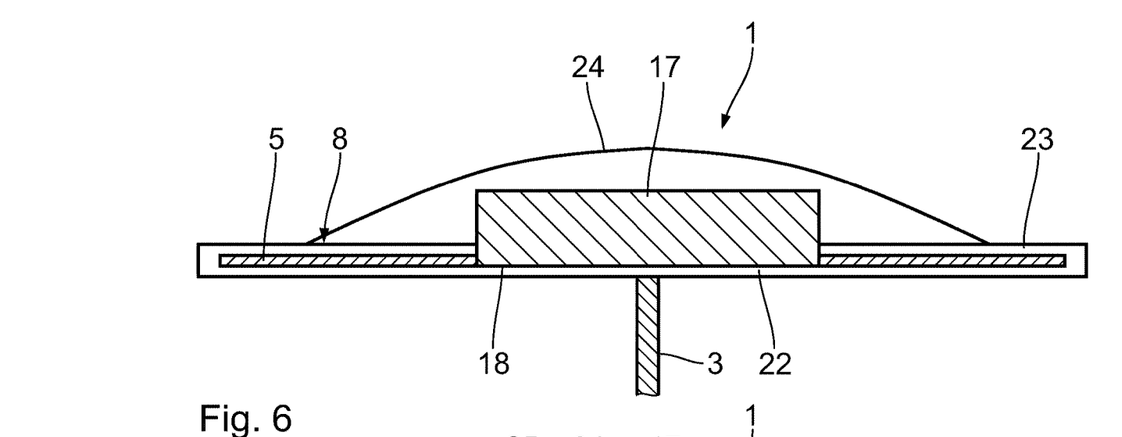
FIG. 6 shows a further configuration of a brain parameter sensor device in a view similar to FIG. 4.

The sensor device 1 according to FIG. 6, in comparison to the sensor device according to FIGS. 4 and 5, has no shell-shaped cover configured in a complementary manner to the electronics housing 17, but a convex cover 24 made of ceramic or titanium. The latter arches over the portion of the electronics housing 17 projecting upwardly over the flexible board 5 in FIG. 6 and seals at the edge against the biocompatible embedding 23 on the flexible board 5.

A further configuration of a brain parameter sensor device 1 will be described below with the aid of FIG. 7. Components, which correspond to those which have already been described above with reference to the configurations according to FIGS. 1 to 6, have the same reference numerals and will not be discussed again in detail.

Figure 7:
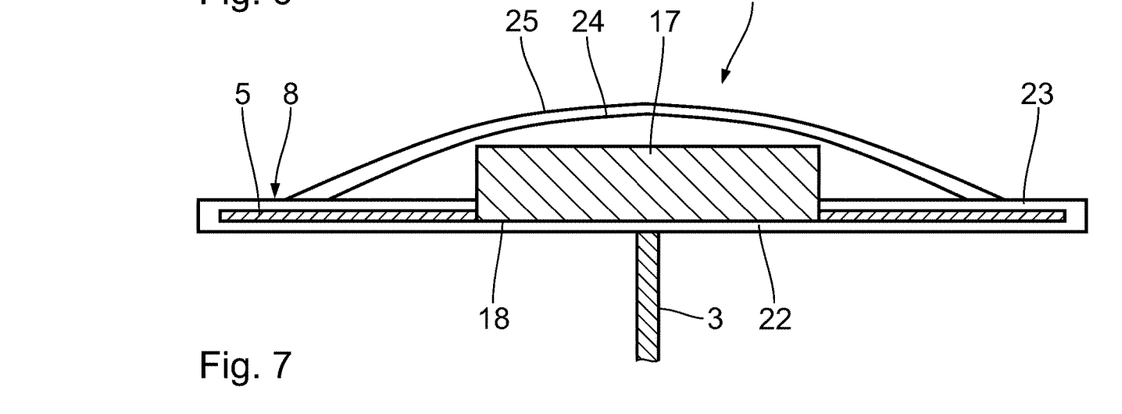
FIG. 7 shows a further configuration of a brain parameter sensor device in a view similar to FIG. 4.

In contrast to the configuration according to FIG. 6, the cover 24 according to FIG. 7 has an additional outer coating 25 made of biocompatible material, in other words also made of silicone or polyurethane. The coating 25 seals at the edge against the embedding 23 of the flexible board 5. As an alternative to a one-sided coating of the convex cover 24, the latter may also be embedded in biocompatible material, in other words, for example, in silicone or polyurethane and be completely enveloped by this embedding, as described above using the example of the flexible board 5.

The invention claimed is:

1. A brain parameter sensor device (1; 16)
with an implantable brain parameter sensor (2),
with an implantable data transmission mechanism (4), which is in signal connection with the brain parameter sensor (2),
wherein the data transmission mechanism (4)
has an antenna (11) for telemetric data transmission to an external data collection unit,
a carrier plate (5, 7) for electronic components (9, 10),
wherein the electronic components (9, 10) on the carrier plate (5, 7) are covered at least to one side by a cover in the form of a membrane,
wherein the entirety of the cover (14) is made from a flexible material, and wherein an edge region of the cover (14) is connected to the carrier plate (5, 7),
wherein the antenna (11) is arranged in an edge region (8) of the carrier plate (5, 7) and is configured running around the latter and around the electronic components (9, 10), and
wherein the antenna is configured as a part of a flexible antenna layer (11), and said flexible antenna layer is connected in a planar manner to the carrier plate (5, 7) and surrounds the carrier plate (5, 7) at the edge.

2. A sensor device according to claim 1, wherein the electronic components (9, 10) on the carrier plate (5, 7) are covered toward both sides by a respective cover (14; 24) formed convexly at least in portions.

3. A sensor device according to claim 2, wherein the cover (24) is produced from one of ceramic and titanium.

4. A sensor device according to claim 1, wherein the antenna (11) is circular.

5. A sensor device according to claim 1 wherein the carrier plate (5, 7) is configured in two layers with two carrier layers, between which the antenna layer (11) is arranged.

6. A sensor device according to claim 1, wherein the antenna (11) is configured as a printed circuit.

7. A sensor device according to claim 1, wherein the carrier plate (5, 7) is covered, where it would be accessible from the outside, by at least one of a coating and an embedding (23) made of a biocompatible material.

8. A sensor device according to claim 7, wherein the coating or the embedding (23) is made by one of the group of silicone, silicone rubber, parylene and polyurethane.

9. A sensor device according to claim 1, wherein the sensor (2) is disposed outside of the cover (14).

10. A sensor device according to claim 1,
wherein the cover (14) is connected to a flexible carrier layer (5) of the carrier plate (5, 7).

11. A brain parameter sensor device (1; 16)
with an implantable brain parameter sensor (2),
with an implantable data transmission mechanism (4), which is in signal connection with the brain parameter (2),
wherein the data transmission mechanism (4)
has an antenna (11) for telemetric data transmission to an external data collection unit,
a carrier plate (5, 7) for electronic components (9, 10),
wherein the electronic components (9, 10) on the carrier plate (5, 7) are covered at least to one side by a cover in the form of a membrane,
wherein the entirety of the cover (14) is made from a flexible material, and wherein an edge region of the cover (14) is connected to the carrier plate (5, 7),
wherein the antenna (11) is arranged in an edge region (8) of the carrier plate (5, 7) and is configured running around the carrier plate (5, 7) and around the electronic components (9, 10),
wherein the carrier plate (5, 7), in an edge region (8) carrying the antenna (11), has a plate thickness (A), which is at most half a thickness (B) measured in the same direction of a region (7) of the carrier plate (5, 7) carrying the electronic components (9, 10),
wherein the antenna (11) is arranged on an upper side of the carrier plate (5, 7).

12. A brain parameter sensor device,
with an implantable brain parameter sensor (2),
with an implantable data transmission mechanism (4), which is in signal connection with the brain parameter sensor (2),
wherein the data transmission mechanism (4)
has an antenna (11) for telemetric data transmission to an external data collection unit,
a carrier plate (5, 7) for electronic components (9, 10),
wherein the electronic components (9, 10) on the carrier plate (5, 7) are covered at least to one side by a cover in the form of a membrane,
wherein the entirety of the cover (14) is made from a flexible material, and wherein an edge region of the cover (14) is connected to the carrier plate (5, 7),
wherein the antenna (11) is arranged in an edge region (8) of the carrier plate (5, 7) and is configured running around the latter and around the electronic components (9, 10), and
wherein the antenna is configured as a part of a flexible antenna layer (11), and said flexible antenna layer is connected in a planar manner to the carrier plate (5, 7) and surrounds the carrier plate (5, 7) at the edge,
wherein said carrier plate (5, 7) comprises a flexible board (5) connected to the sensor (2) by a flexible catheter tube (3), and a rigid board (7) connected to the flexible board on an opposite side from the catheter tube, the rigid board having connected thereto the electronic components (9, 10) on a face of the rigid board opposite to the flexible board,
wherein the antenna (11) is disposed between the rigid board (7) and the flexible board (5), and
wherein the rigid board is larger in diameter than the flexible board.

\* \* \* \* \*